United States Patent
Hara et al.

(10) Patent No.: US 10,357,437 B2
(45) Date of Patent: Jul. 23, 2019

(54) COMPOSITION FOR NANOEMULSION EMULSIFICATION, BICONTINUOUS MICROEMULSION, COSMETIC, AND METHOD FOR PRODUCING SAME

(71) Applicant: NOF CORPORATION, Tokyo (JP)

(72) Inventors: Yusuke Hara, Kanagawa (JP); Kazuaki Wakita, Kanagawa (JP)

(73) Assignee: NOF CORPORATION, Tokyo (JP)

( * ) Notice: Subject to any disclaimer, the term of this patent is extended or adjusted under 35 U.S.C. 154(b) by 50 days.

(21) Appl. No.: 15/556,836

(22) PCT Filed: Mar. 9, 2016

(86) PCT No.: PCT/JP2016/057480
§ 371 (c)(1),
(2) Date: Sep. 8, 2017

(87) PCT Pub. No.: WO2016/147992
PCT Pub. Date: Sep. 22, 2016

(65) Prior Publication Data
US 2018/0049956 A1   Feb. 22, 2018

(30) Foreign Application Priority Data

Mar. 13, 2015  (JP) .................. 2015-050588

(51) Int. Cl.
| | | |
|---|---|---|
| *A61K 8/06* | (2006.01) | |
| *A61K 8/34* | (2006.01) | |
| *A61K 8/81* | (2006.01) | |
| *A61K 8/92* | (2006.01) | |
| *A61Q 19/00* | (2006.01) | |
| *A61Q 5/00* | (2006.01) | |
| *B01J 13/00* | (2006.01) | |
| *A61K 8/37* | (2006.01) | |

(52) U.S. Cl.
CPC .............. *A61K 8/068* (2013.01); *A61K 8/062* (2013.01); *A61K 8/345* (2013.01); *A61K 8/37* (2013.01); *A61K 8/375* (2013.01); *A61K 8/8152* (2013.01); *A61K 8/92* (2013.01); *A61Q 5/00* (2013.01); *A61Q 19/00* (2013.01); *A61Q 19/007* (2013.01); *B01J 13/00* (2013.01); *A61K 2800/413* (2013.01); *A61K 2800/5422* (2013.01)

(58) Field of Classification Search
CPC ...... A61K 2800/413; A61K 2800/5422; A61K 8/062; A61K 8/345
See application file for complete search history.

(56) References Cited

U.S. PATENT DOCUMENTS 6,193,986 B1 * 2/2001 Sakurada

FOREIGN PATENT DOCUMENTS

| JP | H 1190211 A | 4/1999 |
|---|---|---|
| JP | 2000-119130 A | 4/2000 |
| JP | 2004-175682 A | 6/2004 |
| JP | 2005-306760 A | 11/2005 |

(Continued)

OTHER PUBLICATIONS

Machine Translation for JP 2005-306760 A, Published Nov. 4, 2005 (Year: 2005).*

(Continued)

*Primary Examiner* — Alma Pipic
(74) *Attorney, Agent, or Firm* — Muncy, Geissler, Olds & Lowe, P.C.

(57) ABSTRACT

A nanoemulsion emulsification composition including the following components (A) to (D), in which the mass ratios of the components satisfy the following condition,

[(A)+(B)]:(C):(D)=1:4 to 8:0.4 to 0.8;

component (A) is a copolymer including a constitutional unit (a1) represented by Formula (1) and a constitutional unit (a2) represented by Formula (2), the molar ratio of the constitutional units (a1):(a2) being 5:95 to 60:40, and the weight average molecular weight being 5,000 to 5,000,000;

[Chem. 1]

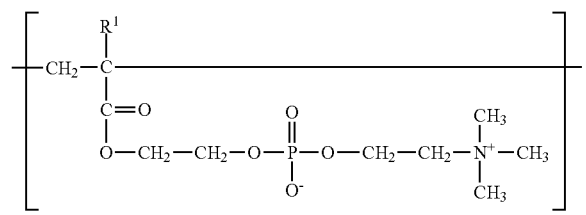

(1)

$R^1$ represents a hydrogen atom or a methyl group

[Chem. 2]

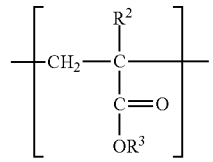

(2)

$R^2$ represents a hydrogen atom or a methyl group, and $R^3$ represents a hydrocarbon group having 12 to 24 carbons;
component (B) is a nonionic surfactant having an HLB value of 10 to 14, component (C) is a polyhydric alcohol, and component (D) is water.

2 Claims, No Drawings

(56) References Cited

FOREIGN PATENT DOCUMENTS

| | | |
|---|---|---|
| JP | 2005-336100 A | 12/2005 |
| JP | 2009-062547 A | 3/2009 |

OTHER PUBLICATIONS

Table 1 from the reference Kunieda, Aramaki. Oleoscience, The Japan Oil Chemists' Society, vol. 1, No. 2, p. 179-186(2001) (Year: 2001).*

* cited by examiner

COMPOSITION FOR NANOEMULSION EMULSIFICATION, BICONTINUOUS MICROEMULSION, COSMETIC, AND METHOD FOR PRODUCING SAME

BACKGROUND OF THE INVENTION

1. Field of the Invention

The present invention relates to a nanoemulsion emulsification composition which can be used for preparing an oil-in-water type emulsion at nano-level particle sizes, a bicontinuous microemulsion and a cosmetic obtained using the composition, and a method for producing this cosmetic.

2. Description of the Related Art

It is known that, because the structures of phosphorylcholine group-containing polymers are similar to those of phospholipids constituting biological membranes, they have excellent biocompatibility, such as in terms of hemocompatibility, complement inactivation, non-adsorption of biological substances and the like, and excellent properties such as antifouling and moisture retention properties, and thus research and development is actively underway in relation to the synthesis of, and applications for, polymers directed to development of bio-related materials, which take advantage of these various functions.

Among these, Patent Literature 1 describes polymer nanosphere employing a copolymer of 2-((meth)acryloyloxy)ethyl-2'-(trimethylammonio)ethyl phosphate and octadecyl methacrylate (hereinafter this copolymer and derivatives thereof are abbreviated as "MPC-based copolymers"), and discloses that a cosmetic including these polymer nanospheres has good tactile feel on the skin, and that the skin is given high water resistance after application, while the barrier function and the moisture retention property thereof are maintained for long periods of time.

Furthermore, Patent Literature 1 suggests that these polymer nanospheres can contain vitamins, various fragrances and the like, thereby improving the usage feel and stability of the substances contained. However, in Patent Literature 1, the types and amounts of the substances that can be contained are not specifically made clear.

Patent Literature 2 describes a cosmetic including cationic nano/fine particles comprising an MPC-based copolymer (polymer nanospheres) and a cationic surfactant, and describes that adsorption to the hair and skin is improved by combining the cationic surfactant with the polymer nanospheres. However, the polymer nanospheres described in Patent Literature 2 does not improve the function of containing liposoluble components, and the amount of liposoluble components that can be contained is very small, which is insufficient.

Patent Literature 3 describes an O/W type emulsion resulting from combining an MPC-based copolymer and a nonionic surfactant. However, the MPC-based copolymer does not form polymer nanospheres in this O/W type emulsion, and improvements in the usage feel and stability of the liposoluble components are not achieved. Furthermore, there is a problem that high pressures of 40 MPa or more are necessary in preparing the emulsion.

Thus, the usage feel and stability of the contained substances can be improved by containing oily components in polymer nanospheres. However, in the prior art, there are few types of oily components that can be contained in polymer nanospheres and the amounts contained are very low.

CITATION LIST

Patent Literature

[PTL 1] Japanese Unexamined Patent Application Publication No. 2009-062547 A

[PTL 2] Japanese Unexamined Patent Application Publication No. 2005-336100 A

[PTL 3] Japanese Unexamined Patent Application Publication No. 2004-175682 A

SUMMARY OF THE INVENTION

Technical Problem

The present invention relates to technology for oil-in-water type emulsions including polymer nanospheres, allowing for increases in the types of oily components contained and the amounts of oily component contained, and more specifically relates to an emulsification composition that can be used in preparing such an oil-in-water type emulsion, a bicontinuous microemulsion and a cosmetic obtained using this composition, and a method for producing this cosmetic.

Solution to Problem

As a result of the intensive investigation undertaken in light of the matters described above, the present inventors arrived at the development of an oil-in-water type emulsion (nanoemulsion) emulsification composition including polymer nanospheres allowing for increases in the types of oily components that can be contained, and the amount of oily component that can be contained, by way of combining a component (A), which is an MPC-based copolymer, a component (B), which is a high-HLB nonionic surfactant, a component (C), which is a polyhydric alcohol, and a component (D), which is water, at specific ratios.

Furthermore, the present inventors also found that a bicontinuous microemulsion could be formed by adding this emulsification composition and a component (E), which is an oily component, and found that the usage feel and stability of a nanoemulsion obtained by further diluting this with water were excellent, because large amounts of various oily components can be contained within these polymer nanospheres, and thus completed the present invention.

That is to say, the present invention is as follows.

(1) A nanoemulsion emulsification composition, comprising the following components (A) to (D), wherein: the mass ratios of the components satisfy the following condition.

$$[(A)+(B)]:(C):(D)=1:4 \text{ to } 8:0.4 \text{ to } 0.8;$$

the component (A) is a copolymer comprising a constitutional unit (a1) represented by Formula (1) and a constitutional unit (a2) represented by Formula (2), the molar ratio of the constitutional units (a1):(a2) being 5:95 to 60:40, and the weight average molecular weight being 5,000 to 5,000,000;

[Chem. 1]

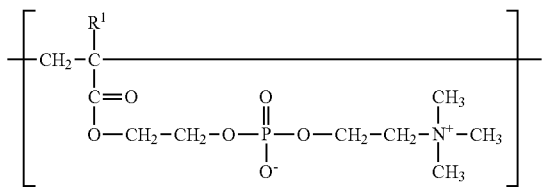

(wherein, $R^1$ represents a hydrogen atom or a methyl group)

[Chem. 2]

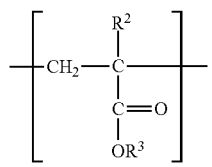

(wherein, $R^2$ represents a hydrogen atom or a methyl group, and $R^3$ represents a hydrocarbon group having 12 to 24 carbons);

the component (B) is a nonionic surfactant having an HLB value of 10 to 14;

the component (C) is a polyhydric alcohol; and the component (D) is water.

(2) A bicontinuous microemulsion obtained by emulsifying the nanoemulsion emulsification composition according to (1) above and a component (E), which is an oily component.

(3) A cosmetic comprising a nanoemulsion obtained by diluting the bicontinuous microemulsion according to (2) above with water.

(4) A method for producing a cosmetic according to (3) above comprising the following steps (I) and (II):

step (I): a step of mixing the nanoemulsion emulsification composition according to (1) above and the component (E) according to (2) above to prepare a bicontinuous microemulsion; and step (II): a step of forming a nanoemulsion by diluting the bicontinuous microemulsion obtained in step (I) with water.

Advantageous Effects of Invention

With the bicontinuous microemulsion comprising the nanoemulsion emulsification composition of the present invention and the oily component (E), it is possible to prepare an oil-in-water type emulsion including polymer nanospheres allowing for increases in the types of oily components contained and the amounts of oily component contained.

Furthermore, the cosmetic of the present invention comprises a nanoemulsion obtained by diluting the bicontinuous microemulsion of the present invention with water, and thus the skin care effects and the hair care effects based on the oily component can be further enhanced to be exhibited and higher stability can be achieved, in comparison to cosmetics including polymer nanospheres in the prior art.

Further, the cosmetic of the present invention can be easily produced with the production method of the present invention.

DETAILED DESCRIPTION OF THE PREFERRED EMBODIMENTS

Embodiments of the present invention will be described below.

(Nanoemulsion Emulsification Composition)

The nanoemulsion emulsification composition of the present invention comprises: a component (A), which is a copolymer; a component (B), which is a nonionic surfactant; a component (C), which is a polyhydric alcohol; and a component (D), which is water. The components are described below. Note that the component (A), the component (B), the component (C) and the component (D) may be referred to as a copolymer (A), a nonionic surfactant (B), a polyhydric alcohol (C) and water (D) respectively.

<Copolymer (A)>

The copolymer (A) used in the present invention comprises a constitutional unit (a1) represented by the Formula (1) and a constitutional unit (a2) represented by the Formula (2).

The constitutional unit (a1) and the constitutional unit (a2) can be respectively derived by polymerizing a phosphorylcholine-like group-containing monomer represented by the following Formula (1') (hereinafter, abbreviated as PC monomer) and a long-chain hydrocarbon group-containing monomer represented by the following Formula (2') (hereinafter, abbreviated as LH monomer). Note that polymerization of the PC monomer and the LH monomer can be performed by known methods.

[Chem. 3]

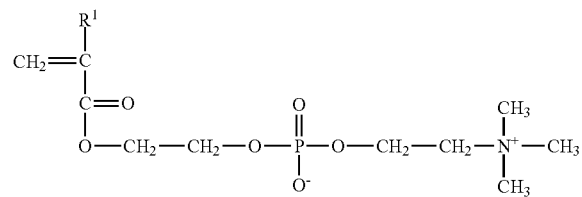

(wherein, $R^1$ represents a hydrogen atom or a methyl group)

Examples of PC monomers include 2-methacryloyloxyethyl phosphorylcholine and 2-acryloyloxyethyl phosphorylcholine. One type selected from among these may be used alone or two or more types may be used in combination, as the PC monomer.

[Chem. 4]

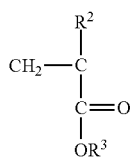

(wherein, $R^2$ represents a hydrogen atom or a methyl group, and $R^3$ represents a hydrocarbon group having 12 to 24 carbons)

$R^3$ in the LH monomer is a long-chain hydrocarbon group having 12 to 24 carbons, preferably 14 to 20 carbons, and particularly preferably 16 to 18 carbons. If the number of carbons in the hydrocarbon group is too low, the water solubility of the copolymer will be high, and it may be difficult to form polymer nanospheres without self-association, in water. Furthermore, if the number of carbons is too high, the particle size of the polymer nanospheres will be large, such that the polymer nanospheres may not stabilize.

The hydrocarbon group may be a saturated or unsaturated hydrocarbon group and may be a linear or branched hydrocarbon group.

Examples of the LH monomer include linear or branched alkyl (meth)acrylates such as decyl (meth)acrylate, dodecyl (meth)acrylate, tetradecyl (meth)acrylate, hexadecyl (meth)acrylate, octadecyl(meth) acrylate, docosanyl (meth)acrylate and the like. Furthermore, one type selected from among these may be used alone or two or more types may be used in combination, as the LH monomer.

The weight average molecular weight of the copolymer (A) is in the range of 5,000 to 5,000,000 and preferably in the range of 10,000 to 1,000,000. If the weight average molecular weight of the copolymer is too low, the stability of the polymer nanospheres may be inferior, while if the weight average molecular weight is too high, it may be difficult to form polymer nanospheres.

Note that, in the present invention, the weight average molecular weight of the copolymer (A) is a value measured by gel permeation chromatography (GPC) under the conditions described in the examples.

Furthermore, the molar ratio of the constitutional units, (a1):(a2), in the copolymer (A) is 5:95 to 60:40, and this molar ratio is also the same for the constitutional molar ratio for the PC monomer and the LH monomer. That is to say, the constitutional molar ratio for the PC monomer and the LH monomer is 5 to 60 mol % of the PC monomer and 40 to 95 mol % of the LH monomer, preferably 15 to 30 mol % of the PC monomer and 70 to 85 mol % of the LH monomer. With a copolymer in which the ratio of the LH monomer is too low, it may be difficult to sufficiently maintain the stability of the polymer nanosphere dispersion, while if the ratio of the LH monomer is too high, it may be difficult to produce the configuration as a polymer nanosphere.

<Nonionic Surfactant (B)>

The hydrophile-lipophile balance (HLB) value of the nonionic surfactant (B) used in the present invention is 10 to 14, and preferably 10.5 to 13.5. If the HLB value is too low or too high, it may be difficult to create a bicontinuous microemulsion, and thus it may be difficult to form an oil-in-water type emulsion at nano-level particle sizes.

The nonionic surfactant (B) used in the present invention is not limited in terms of the type of nonionic surfactant, as long as the HLB value is in the range of 10 to 14. Examples include fatty acid ester type nonionic surfactants such as polyoxyethylene polyol fatty acid esters, polyethylene glycol fatty acid esters, polyglycerol fatty acid esters, and polyoxyethylene hydrogenated castor oil derivatives; alkyl or aryl ether type nonionic surfactants such as polyoxyethylene alkyl ethers, and polyoxyethylene alkyl phenyl ethers; polyoxyethylene-polyoxypropylene block copolymers; polyoxyethylene-polyoxypropylene block copolymer adducts of ethylenediamine; polyoxyethylene alkylamine and the like.

Specific examples of the nonionic surfactant (B) include polyoxyethylene sorbitan fatty acid esters such as polyoxyethylene sorbitan monolaurate, polyoxyethylene sorbitan monopalmitate, polyoxyethylene sorbitan monostearate, polyoxyethylene sorbitan monooleate, polyoxyethylene sorbitan trioleate, and polyoxyethylene sorbitan tetraoleate; polyoxyethylene sorbitol fatty acid esters such as polyoxyethylene sorbitol monolaurate, polyoxyethylene sorbitol monostearate, polyoxyethylene sorbitol tetrastearate, polyoxyethylene sorbitol hexastearate, polyoxyethylene sorbitol monooleate, polyoxyethylene sorbitol tetraoleate, polyoxyethylene sorbitol pentaoleate, polyoxyethylene sorbitol monoisostearate and polyoxyethylene sorbitol tetraisostearate; polyoxyethylene glycerol fatty acid esters such as polyoxyethylene glycerol monostearate, polyoxyethylene glycerol monoisostearate, polyoxyethylene glycerol triisostearate and polyoxyethylene glycerol monooleate; ethylene glycol fatty acid esters such as polyoxyethylene monolaurate, polyoxyethylene monostearate, polyoxyethylene distearate, polyoxyethylene monooleate, polyoxyethylene dioleate, and ethylene glycol distearate; polyoxyethylene alkyl or alkenyl ethers such as polyoxyethylene lauryl ether, polyoxyethylene cetyl ether, polyoxyethylene stearyl ether, polyoxyethylene oleyl ether, polyoxyethylene behenyl ether, and polyoxyethylene 2-octyldodecyl ether; polyoxyethylene hydrogenated castor oil and the like.

Here, the HLB value can be obtained from the following equation proposed by Kawakami (Kawakami: Science, 23,546 (1953)).

$$HLB\ value = 7 + 11.7 \cdot Log(MW/MO)$$

(wherein, MW is the molecular weight of the hydrophilic group, and MO is the molecular weight of the lipophilic group moiety)

Examples of the nonionic surfactant (B) preferably include polyoxyethylene (5 to 9) lauryl ether, polyoxyethylene (6 to 12) cetyl ether, polyoxyethylene (7 to 14) oleyl ether, polyoxyethylene (7 to 14) stearyl ether, polyoxyethylene (5 to 10) alkyl (12 to 14) ether, polyoxyethylene (6 to 10) tridecyl ether, polyoxyethylene (5 to 10) myristyl ether, polyoxyethylene (7 to 12) isostearyl ether, polyoxyethylene (10 to 15) behenyl ether, polyoxyethylene (21 to 26) polyoxypropylene (10 to 15) decyltetradecyl ether, and polyoxyethylene (20 to 40) hydrogenated castor oil.

One type selected from among these may be used alone or two or more types may be used in combination, as the nonionic surfactant (B).

<Polyhydric Alcohol (C)>

The polyhydric alcohol (C) used in the present invention is a dihydric or higher alcohol, and preferably a dihydric or trihydric alcohol. The number of carbons in the polyhydric alcohol (C) is, for example, 2 to 10, and preferably 2 to 6.

Examples of the polyhydric alcohol (C) include ethylene glycol, propylene glycol, dipropylene glycol, 1,3-butylene glycol, glycerol and the like, and 1,3-butylene glycol and glycerol are preferred.

One type selected from among these may be used alone or two or more types may be used in combination, as the polyhydric alcohol (C). For example, a mixed solution comprising 25 to 75 mass % of glycerol and 75 to 25 mass % of 1,3-butylene glycol, in which the total content of glycerol and 1,3-butylene glycol is 100 mass % can be used.

<Water (D)>

The water (D) used in the present invention includes purified water, distilled water, ion-exchanged water and the like.

By including the polyhydric alcohol (C) and water (D) in the nanoemulsion emulsification composition of the present invention, the lipophilicity-hydrophilicity balance of the nonionic surfactant (B) can be adjusted and an infinite association of the nonionic surfactant (B) can be formed. In this infinite association, the mean curvature of the nonionic surfactant (B) becomes zero and the oil phase and the aqueous phase are continuous. This state is called bicontinuous microemulsion.

In the nanoemulsion emulsification composition of the present invention, the mass ratios of the components satisfy the following condition.

$$[(A)+(B)]:(C):(D)=1:4 \text{ to } 8:0.4 \text{ to } 0.8;$$

That is to say, the mass ratio $(C)/[(A)+(B)]$ of the polyhydric alcohol (C) to the total mass of the copolymer (A) and the nonionic surfactant (B) is 4 to 8, and preferably 4 to 5.

The mass ratio $(D)/[(A)+(B)]$ of the water (D) to the total mass of the copolymer (A) and the nonionic surfactant (B) is 0.4 to 0.8, and preferably 0.4 to 0.6.

Outside of these ratio ranges, it may be difficult to obtain nanoemulsion fine particles, because it is difficult to obtain a bicontinuous microemulsion, even if emulsified with the oily component, which is the component (E) described below.

Note that the mass ratio $(A)/(B)$ of the copolymer (A) to the nonionic surfactant (B) is preferably 0.01 to 0.8, and particularly preferably 0.1 to 0.4.

(Bicontinuous Microemulsion)

The bicontinuous microemulsion of the present invention results from emulsifying the nanoemulsion emulsification composition of the present invention and the component (E), which is an oily component. Hereinafter, the oily component that serves as the component (E) may be referred to as the oily component (E).

Components that can be used in ordinary cosmetics can be used as the oily component (E), and examples include hydrocarbon oils, ester oils, vitamins, hormones, phospholipid derivatives, whitening agents, antiinflammatory/antihistaminic agents, antioxidants, intercellular lipids, ultraviolet absorbers, various moisturizers, various perfumes, and the like.

Examples of hydrocarbon oils include liquid paraffin, polybutene, hydrogenated polyisobutene, hydrogenated polydecene, squalane, squalene, pristane, light isoparaffin, light liquid isoparaffin, heavy liquid isoparaffin, tetradecene, isohexadecane, isododecane, α-olefin oligomers, petroleum jelly, microcrystalline wax, paraffin, polyethylene, ceresin and the like.

Ester oils are oils having an ester group, and examples include triglycerides of a fatty acid and glycerol, oils and fats, as well as esters of amino acids or fatty acids and monohydric or higher alcohols.

Examples of the fatty acids used to form the triglyceride include caproic acid, caprylic acid, capric acid, 2-ethylhexanoic acid, lauric acid, tridecanoic acid, isotridecanoic acid, myristic acid, palmitic acid, isopalmitic acid, stearic acid, isostearic acid, eicosanoic acid, behenic acid, tetracosanoic acid, myristoleic acid, palmitoleic acid, oleic acid, elaidic acid, erucic acid, linoleic acid, linolenic acid, arachidonic acid, hydroxystearic acid, coconut oil fatty acid, palm kernel oil fatty acid, hydrogenated palm kernel oil fatty acid, palm oil fatty acid, beef tallow fatty acid, hydrogenated beef tallow fatty acid, lard fatty acid, castor oil fatty acid, hydrogenated castor oil fatty acid and the like.

Examples of oils and fats include oils and fats such as olive oil, sunflower oil, palm oil, palm kernel oil, safflower oil, castor oil, hydrogenated castor oil, coconut oil, *camellia* oil, cocoa butter, shea butter and the like.

Examples of esters of amino acids and monohydric or higher alcohols include, dihexyldecyl N-lauroyl-L-glutamate, isopropyl lauroyl sarcosinate, diisostearyl N-lauroyl-L-glutamate, bis (hexyldecyl/octyldodecyl) N-lauroyl-L-glutamate, dioctyldodecyl N-lauroyl-L-glutamate, dioctyldodecyl N-stearoyl-L-glutamate, N-myristoyl-N-methyl-β-alanine phytosteryl, di(cholesteryl/behenyl/2-octyldodecyl) N-lauroyl-L-glutamate, di(phytosteryl/behenyl/2-octyldodecyl) N-lauroyl-L-glutamate, di(cholesteryl/2-octyldodecyl) N-lauroyl-L-glutamate, di(phytosteryl/2-octyldodecyl) N-lauroyl-L-glutamate, di(phytosteryl/behenyl/2-octyldodecyl/isostearyl) N-lauroyl-L-glutamate and the like.

Examples of esters of fatty acids and monohydric or higher alcohols include ethyl oleate, ethyl linoleate, isopropyl myristate, isopropyl palmitate, isopropyl isostearate, isopropyl lanolate, cetyl 2-ethylhexanoate, isocetyl 2-ethylhexanoate, stearyl 2-ethylhexanoate, isostearyl 2-ethylhexanoate, cetyl palmitate, 2-ethylhexyl palmitate, 2-hexyldecyl isostearate, isostearyl isostearate, trimethylolpropane triisostearate, myristyl myristate, cetyl myristate, octyldodecyl myristate, isostearyl myristate, isocetyl myristate, hexyl laurate, decyl oleate, octyldodecyl oleate, isostearyl pivalate, isopropyl isostearate, isononyl isononanoate, 2-ethylhexyl isononanoate, isodecyl isononanoate, isotridecyl isononanoate, octyldodecyl erucate, neopentyl glycol didecanoate, pentaerythrityl tetraethylhexanoate, diisostearyl malate, didecyl adipate, glyceryl isostearate, hydrogenated castor oil isostearate, cholesteryl isostearate, batyl isostearate, phytosteryl isostearate, octyl oxystearate, dihydrocholesteryl oleate, phytosteryl oleate, hydrogenated castor oil stearate, cholesteryl lanolate, cholesteryl hydroxystearate, phytosteryl hydroxystearate, dipentaerythritol hexahydroxystearate, hydrogenated castor oil monohydroxystearate, isostearyl lanolate, isopropyl lanolate, octyldodecyl lanolate, cholesteryl stearate, cholesteryl lanolate, cetyl ricinoleate, dioctyl succinate, cetyl lactate, propylene glycol dicaprylate, propylene glycol dicaprate, propylene glycol dinonanoate, propylene glycol di(caprylate/caprate), propylene glycol distearate, propylene glycol diisostearate, propylene glycol dioleate, (phytosteryl/isostearyl/cetyl/stearyl/behenyl) dimer dilinoleate and the like. Furthermore, waxes such as beeswax, *Rhus succedanea* fruit wax, carnauba wax, lanolin, candelilla wax and jojoba oil can be used.

One type selected from among these may be used alone or two or more types may be used in combination, as the ester oil.

Examples of preferred ester oils include, triglycerides of fatty acids having 6 or more carbons such as glyceryl tri(caprylate/caprate), oils and fats, cetyl 2-ethylhexanoate, isocetyl 2-ethylhexanoate, isopropyl palmitate, 2-ethylhexyl palmitate, isopropyl isostearate, 2-hexyldecyl isostearate, octyldodecyl myristate, isopropyl myristate, isostearyl myristate, isocetyl myristate, isononyl isononanoate, 2-ethylhexyl isononanoate, isodecyl isononanoate, isotridecyl isononanoate, beeswax, *Rhus succedanea* fruit wax, phytosteryl hydroxystearate, N-myristoyl-N-methyl-β-alanine phytosteryl, di(cholesteryl/behenyl/2-octyldodecyl) N-lauroyl-L glutamate, di(phytosteryl/behenyl/2-octyldodecyl) N-lauroyl-L-glutamate, di(cholesteryl/2-octyldodecyl) N-lauroyl-L-glutamate, di(phytosteryl/2-octyldodecyl) N-lauroyl-L-glutamate, di(phytosteryl/behenyl/2-octyldodecyl/isostearyl) N-lauroyl-L-glutamate, (phytosteryl/isostearyl/cetyl/stearyl/behenyl) dimer dilinoleate and the like.

Examples of vitamins include vitamin A and derivatives thereof, oil-soluble vitamin B2 derivatives, oil-soluble vitamin B6 derivatives, oil-soluble vitamin C derivatives, amphiphilic vitamin C derivatives such as trisodium ascorbyl palmitate phosphate, vitamin D, vitamin E and derivatives thereof such as tocopherols and tocopherol acetate, vitamin H, oil-soluble pantothenic derivatives, coenzyme Q10 (vitamin Q), and the like.

Examples of hormones include cortisone, hydrocortisone, estradiol, estrone and the like.

Examples of phospholipid derivatives include cyclic lysophosphatidic acid, cyclic lysophosphatidic acid sodium salt, mixtures of cyclic lysophosphatidic acid and cyclodextrin (the ratio by mass being 1:1, for example), and the like.

Examples of whitening agents include kojic acid, placenta extract, arbutin, ellagic acid, rucinol, linoleic acid and the like.

Examples of anti-inflammatory agents/antihistamines include glycyrrhetinic acid and derivatives thereof, glycyrrhizic acid and derivatives thereof, allantoin, hydrocortisone acetate, prednisolone and the like.

Examples of antioxidants (aging inhibitors) include polyphenols, carotenoids, flavonoids, N-methyl-L-serine, tranexamic acid, ursolic acid and the like.

Examples of intercellular lipids include ceramide, cholesterol and the like.

Examples of ultraviolet absorbers include para-aminobenzoic acid derivatives, cinnamic acid derivatives, benzophenone derivatives, salicylic acid derivatives and the like.

Examples of moisturizers include hyaluronic acid derivatives such as sodium hyaluronate, collagen derivatives, elastin derivatives, keratin derivatives and the like.

Examples of fragrances include various plant extracts such as orange peel extract and apricot juice, having flavonoids as principle components, limonene and the like.

One type selected from among these oily components may be used alone or two or more types may be used in combination.

Among these oily components (E), with a view to the amount that can be contained by the copolymer (A) being great, which is to say, the mass ratio of (E)/(A) being great, those having an average molecular weight of 510 g/mol or more are preferred, and those having an average molecular weight of 550 g/mol or more are particularly preferred. Specific examples include trisodium ascorbyl palmitate phosphate, di(phytosteryl/octyldodecyl) lauroyl glutamate, di(octyldodecyl/phytosteryl/behenyl) lauroyl glutamate, (phytosteryl/isostearyl/cetyl/stearyl/behenyl) dimer dilinoleate, mixtures of cyclic lysophosphatidic acid and cyclodextrin (the mass ratio being 1:1, for example), glycyrrhizic acid, ceramides, and orange peel extract having flavonoids as principal components, and the like.

The amount of the oily component (E) admixed varies depending on the type of the oily component (E), but is usually 0.1 to 50 parts by mass, preferably 1 to 20 parts by mass, and particularly preferably, 2 to 10 parts by mass, with respect to 100 parts by mass of the nanoemulsion emulsification composition.

(Cosmetic)

The cosmetic of the present invention comprises a nanoemulsion obtained by diluting the bicontinuous microemulsion of the present invention with water.

The amount of water used for dilution is, for example, from 50 to 99.9% by mass, and preferably from 80 to 97% by mass, with respect to the overall cosmetic.

When the nanoemulsion is taken as 100 mass %, the amount of the oily component (E) blended is preferably such as to be diluted to 0.1 to 1.0 mass %, and particularly preferably 0.2 to 0.5 mass %.

The cosmetic of the present invention is preferably produced by a method having the following steps (I) and (II).

step (I): a step of forming a bicontinuous microemulsion by mixing and emulsifying a nanoemulsion emulsification composition containing the components (A), (B), (C) and (D) at the above mass ratios and the oily component (E)

step (II): a step of forming a nanoemulsion by diluting the bicontinuous microemulsion obtained in step (I) with water.

By forming the bicontinuous microemulsion in step (I), the amount of oily component (E) contained in the polymer nanospheres can be increased.

The bicontinuous microemulsion is formed by mixing components (A) to (E) and stirring, usually at 1 to 95° C. and preferably at 10 to 90° C.

In the same manner as the water (D), purified water, distilled water, ion-exchanged water and the like can be mentioned as the water used for dilution in the step (II). The temperature when diluting with water is usually 1 to 95° C., preferably room temperature (1 to 30° C.), and particularly preferably 15 to 25° C.

The particle size of the nano/fine particles that constitute the nanoemulsion obtained by the present invention is preferably 5 to 500 nm, but with a view to enhancing the usage feel of the cosmetic, 300 nm or less is more preferable. If the particle size of the nano/fine particles is too great, there is a tendency towards aggregation, such that the stability of the dispersion is inferior, and when used in cosmetics, this tends to feel rough. If the particle size of the nano/fine particles is too low, the stability may be inferior.

Note that, the particle size of the nano/fine particles included in the cosmetic of the present invention can be measured, for example, by employing a principle such as a dynamic light scattering, using equipment such as a commercially available particle size distribution measuring device, and the average particle size measured by these methods can be considered the particle size of the nanoparticles referred to in the present invention. The average particle size is calculated based on the average value of a volume/particle size distribution function, assuming the distribution function to have a Gaussian distribution. Furthermore, the particle size of the nano/fine particles can be adjusted to 5 to 500 nm by appropriately performing the method for producing nanoparticles describe above.

In addition to the nano/fine particles, additives that are commonly used in cosmetics can be suitably blended in the cosmetic of the present invention, as necessary. There are no particular limitations on the aforementioned additives as long as they do not detract from object of the present invention, and examples thereof include moisturizers, thickeners, antioxidants, preservatives, pH adjusters, perfumes and the like.

In particular, when a fatty acid such as isostearic acid is added, a bicontinuous microemulsion is readily formed, which is desirable as it allows for increases in the types of oily components contained and the amounts of oily component contained. Furthermore, if a mucopolysaccharide such as hyaluronic acid is added, the stability of the contained oily component is somewhat increased, and moisture retention is achieved and a moist tactile feel is produced, which is desirable.

EXAMPLES

Hereafter, the present invention will be described in concrete terms by way of the examples and comparative examples.

The amounts blended in the examples and comparative examples are given in mass %. The term remainder refers to a numerical value such that the sum of all components is 100 mass %.

Hereafter, the method of measuring the weight average molecular weight of various copolymers is described.

The molecular weight of the copolymer was measured under the following gel permeation chromatography (GPC) conditions.

Sample polymers were dissolved in a chloroform/methanol (=6/4, volume ratio) mixed solvent including 0.5 mass % of lithium bromide, to prepare a 0.5% mass solution.

(GPC Analysis Conditions)

Columns: PL gel 5 μm MIXED-C, two in series (made by Polymer Laboratories Ltd.); elution solvent: chloroform/methanol (=6/4, volume ratio) mixed solvent including 0.5 mass % lithium bromide; detection: differential refractometer; reference material for measuring weight average molecular weight (Mw): PMMA (made by Polymer Laboratories Ltd.); flow rate: 1.0 mL/min; amount of sample solution used: 20 μL; column temperature: 40° C.; a molecular weight calculation program with built-in integrator made by Tosoh Corporation (GPC program for SC-8020) was used.

When the weight average molecular weight of a Lipidure-NR (2-methacryloyloxyethyl phosphorylcholine/stearyl methacrylate) copolymer (made by NOF Corporation) (molar ratio of constitutional units (a1):(a2)=33:67) was measured according to the method, this was 189,000.

Examples 1 to 21 and Comparative Examples 1 to 6

Emulsification compositions and cosmetics were produced by the following production method, with the compositions set forth in Tables 1 to 4, and the storage stability of the cosmetics were evaluated. The results are shown together in Tables 1 to 4.

Examples 22 and 23 and Comparative Examples 7 to 10

Emulsification compositions and cosmetics were produced by the following production method, with the compositions set forth in Tables 5 and 6, and the storage stability of the cosmetics were evaluated. The results are shown together in Tables 5 and 6.

<Production Method>

Step I: The materials shown under step I in the tables were charged into a beaker and stirred at 60° C. with a stirrer.

Step II: The compositions prepared in step I were diluted with water at room temperature to obtain a cosmetic comprising an O/W emulsion.

<Stability>

The cosmetics produced were filled into 100 cc screw tubes, at 50 g each, and after sealing, these were stored at room temperature. The appearances of the samples were checked immediately after production, on the day after production, one week after production, and one month after production (only for Examples), and evaluated according to the following criteria.

○ (good): pale translucent solution x (poor): solution with creaming or settling In the tables, label name: glycerol, BG is a solution in which mass ratio of glycerol to 1,3-butanediol is 1:1.

The mass ratios for the components (A), (B), (C) and (D) of the emulsification composition are shown in the tables as (A)+(B):(C):(D). When the component (A') was used in place of the component (A), and when the component (B') was used in place of the component (B), the mass ratios with replacement by these components are given.

Label names, product names, and ingredient names of some of the materials used in the examples and comparative examples are described below.

Label name: Polyquaternium-61 (made by NOF Corporation; product name: LIPIDURE-NR; ingredient name: (2-methacryloyloxyethyl phosphorylcholine/stearyl methacrylate) copolymer, glycerol, BG)

Label name: PPG-13 Decyltetradeceth-24 (HLB=10.7) (made by NOF Corporation; product name: UNILUBE 50MT-2200B; ingredient name: polyoxyethylene (24) polyoxypropylene (13) decyltetradecyl ether)

Label name: di(phytosteryl/octyldodecyl)lauroyl glutamate (made by AJINOMOTO HEALTHY SUPPLY CO., INC.; product name: ELDEW PS-203)

Label name: hydrogenated polyisobutene (made by NOF Corporation; product name: PARLEAM EX)

Label name: trisodium ascorbyl palmitate phosphate (made by Showa Denko K.K.; product name: Apprecier)

Label name: glyceryl tri(caprylate/caprate) (made by NOF Corporation; product name: Panasate 810)

Label name: cyclic lysophosphatidic acid, cyclodextrin (made by NOF Corporation; product name: CyPA-PW)

Label name: Ceramide 2 (made by Takasago International Corporation; product name: Ceramide TIC-001)

Label name: isopropyl lauroyl sarcosinate (made by AJINOMOTO HEALTHY SUPPLY CO., INC.; product name: ELDEW SL-205)

Label name: di(octyldodecyl/phytosteryl/behenyl)lauroyl glutamate (made by AJINOMOTO HEALTHY SUPPLY CO., INC.; product name: ELDEW PS-306)

Label name: (phytosteryl/isostearyl/cetyl/stearyl/behenyl) dimer dilinoleate (made by Nippon Fine Chemical Co., Ltd.; product name: Plandool-S, H)

Label name: Orange peel extract (made by NOF Corporation; product name: CHINPI EXTRACT PM-F)

Label name: sodium hyaluronate (made by Kewpie Corp.; product name: hyaluronic acid HA-Q)

Label name: cocoyl arginine ethyl PCA (made by AJINOMOTO HEALTHY SUPPLY CO., INC.; product name: CAE)

Note that label name: cyclic lysophosphatidic acid, cyclodextrin is a mixture in which the mass ratio of cyclic lysophosphatidic acid to cyclodextrin is 1:1, and the average molecular weight is calculated based on the mass ratio. Further, the average molecular weight of label name: orange peel extract is the molecular weight of the flavonoids that are the main components.

In Table 4, the polymer powders of Polyquaternium-52 and polymethacryloylethyl phosphorylcholine were produced according to the following methods.

Synthesis Example 1

Product name: Lipidure-PMB (made by NOF Corporation) was freeze-dried to obtain a polymer powder of Polyquaternium-52 (ingredient name: (2-methacryloyloxyethyl phosphorylcholine/butyl methacrylate) copolymer (molar ratio of constitutional units (a1):(a2)=80:20))

Synthesis Example 2

Product name: Lipidure-HM (made by NOF Corporation) was freeze-dried to obtain a polymer powder of polymethacryloylethyl phosphorylcholine.

In Table 5, label name: (C12-14) Pareth-7 (HLB=12.3), (made by NOF Corporation; product name: Nonion NC-207; ingredient name: polyoxyethylene (7) alkyl (12 to 14) ether) and label name: polyoxyethylene hydrogenated castor oil (HLB=13.3) (made by NOF Corporation; product name: UNIOX HC-40; ingredient name: polyoxyethylene (40) hydrogenated castor oil) were used.

In Table 6, Label name: Myreth-3 (HLB=7.6) (made by NOF Corporation; product name: Nonion M-203; ingredient name: polyoxyethylene (3) myristyl ether); label name: (C12-14) Pareth-3 (HLB=8.1) (made by NOF Corporation; product name: Nonion NC-203; ingredient name: polyoxyethylene (3) alkyl (12 to 14) ether); label name: Myreth-4 (HLB=9.0) (made by NOF Corporation; product name: Nonion M-204; ingredient name: polyoxyethylene (4) myristyl ether); and label name: (C12-14) Pareth-12 (HLB=14.6) (made by NOF Corporation; product name: Nonion NC-212; ingredient name: polyoxyethylene (12) alkyl (12 to 14) ether) were used.

TABLE 1

| Step | Component | Label name | Product name | Average molecular weight of (E) (g/mol) | Ex. 1 | Ex. 2 | Ex. 3 | Ex. 4 | Ex. 5 | Ex. 6 | Ex. 7 |
|---|---|---|---|---|---|---|---|---|---|---|---|
| I | (A) | Polyquaternium-61 | Lipidure-NR | — | 0.1 | 0.2 | 0.2 | 0.1 | 0.1 | 0.1 | 0.1 |
| | (C) | glycerol, BG | — | — | 1.9 | 3.8 | 3.8 | 1.9 | 1.9 | 1.9 | 1.9 |
| | (B) | PPG-13 Decyltetradeceth-24 (HLB = 10.7) | UNILUBE 50MT-2200B | — | 0.5 | 0.5 | 0.7 | 0.5 | 0.5 | 0.5 | 0.5 |
| | (C) | glycerol | — | — | 0.6 | 0.6 | 0.6 | 0.6 | 0.6 | 0.6 | 0.6 |
| | (D) | water | — | — | 0.4 | 0.4 | 0.5 | 0.4 | 0.4 | 0.4 | 0.4 |
| | (E) | tocopherol acetate | — | 472 | 0.1 | 0.1 | 0.2 | 0.3 | — | — | — |
| | | di(phytosteryl/octyldodecyl) lauroyl glutamate | ELDEW PS-203 | 1025 | — | — | — | — | 0.5 | 0.5 | — |
| | | octyldodecyl myristate | octyldodecyl myristate | 500 | — | — | — | — | — | — | 0.1 |
| | | hydrogenated polyisobutene | PARLAM EX | 490 | — | — | — | — | — | — | — |
| | | limonene | — | 136 | — | — | — | — | — | — | — |
| | | trisodium ascorbyl palmitate phosphate | — | 560 | — | — | — | — | — | — | — |
| | | glyceryl tri(caprylate/caprate) | Apprecier | 465 | — | — | — | — | — | — | — |
| | | cyclic lysophosphatidic acid | Panasate 810 | 678 | — | — | — | — | — | — | — |
| | | cyclodextrin | CyPA-PW | — | — | — | — | — | — | — | — |
| | | ceramide 2 | Ceramide TIC-001 | 555 | — | — | — | — | — | — | — |
| | | glycyrrhizic acid | — | 822 | — | — | — | — | — | — | — |
| | | glycyrrhetinic acid | — | 470 | — | — | — | — | — | — | — |
| | | isopropyl lauroyl sarcosinate | ELDEW SL-205 | 314 | — | — | — | — | — | — | — |
| | | di(octyldodecyl/phytosteryl/behenyl) lauroyl glutamate | ELDEW PS-306 | 1000 | — | — | — | — | — | — | — |
| | | tranexamic acid | — | 157 | — | — | — | — | — | — | — |
| | | (phytosteryl/isostearyl/cetyl/stearyl/behenyl) dimer dilinoleate | Plandool-S, H | 1180 | — | — | — | — | — | — | — |
| | | orange peel extract | CHINPI EXTRACT PM-F | — | — | — | — | — | — | — | — |
| | other | isostearic acid | — | — | — | — | — | — | 0.1 | — | — |
| | | sodium hyaluronate | hyaluronic acid HA-Q | 580 | — | — | — | — | — | 0.1 | — |
| II | water | water | — | | remainder | remainder | remainder | remainder | remainder | remainder | remainder |
| | | (E)/(A) | | | 1 | 0.5 | 1 | 3 | 5 | 5 | 1 |
| | | (A + B):(C):(D) | | | 10:41.6:6.6 | 10:62.8:5.7 | 10:49.3:5.5 | 10:41.6:6.6 | 10:41.6:6.6 | 10:41.6:6.6 | 10:41.6:6.6 |
| | | O/W emulsion appearance * (immediately after production) | | | ○ | ○ | ○ | ○ | ○ | ○ | ○ |
| | | O/W emulsion appearance (ambient termperature, next day) | | | ○ | ○ | ○ | ○ | ○ | ○ | ○ |
| | | O/W emulsion appearance (ambient termperature, one week later) | | | ○ | ○ | ○ | ○ | ○ | ○ | ○ |
| | | O/W emulsion appearance (ambient termperature, one month later) | | | ○ | ○ | ○ | ○ | ○ | ○ | ○ |

TABLE 2

| Step | Component | Label name | Product name | Average molecular weight of (E) (g/mol) | Ex. 8 | Ex. 9 | Ex. 10 | Ex. 11 | Ex. 12 | Ex. 13 | Ex. 14 |
|---|---|---|---|---|---|---|---|---|---|---|---|
| I | (A) | Polyquaternium-61 | Lipidure-NR | — | 0.1 | 0.1 | 0.1 | 0.1 | 0.1 | 0.1 | 0.1 |
| | (C) | glycerol, BG | — | — | 1.9 | 1.9 | 1.9 | 1.9 | 1.9 | 1.9 | 1.9 |
| | (B) | PPG-13 Decyltetradeceth-24 (HLB = 10.7) | UNILUBE 50MT-2200B | — | 0.5 | 0.5 | 0.5 | 0.5 | 0.5 | 0.5 | 0.5 |
| | (C) | glycerol | — | — | 0.6 | 0.6 | 0.6 | 0.6 | 0.6 | 0.6 | 0.6 |
| | (D) | water | — | — | 0.4 | 0.4 | 0.4 | 0.4 | 0.4 | 0.4 | 0.4 |
| | (E) | tocopherol acetate | — | 472 | — | — | — | — | — | — | — |
| | | di(phytosteryl/octyldodecyl) lauroyl glutamate | ELDEW PS-203 | 1025 | — | — | — | — | — | — | — |
| | | octyldodecyl myristate | octyldodecyl myristate | 500 | 0.3 | — | — | — | — | — | — |
| | | hydrogenated polyisobutene | PARLAM EX | 490 | — | — | — | — | — | — | — |
| | | limonene | — | 136 | — | — | — | — | — | — | — |
| | | trisodium ascorbyl palmitate phosphate | — | 560 | — | 0.1 | — | — | — | — | — |
| | | glyceryl tri(caprylate/caprate) | Apprecier | 465 | — | — | 0.1 | — | — | — | — |
| | | cyclic lysophosphatidic acid | Panasate 810 | 678 | — | — | — | 0.4 | — | — | — |
| | | cyclodextrin | CyPA-PW | | — | — | — | — | 0.2 | — | — |
| | | ceramide 2 | Ceramide TIC-001 | 555 | — | — | — | — | — | — | 0.5 |
| | | glycyrrhizic acid | — | 822 | — | — | — | — | — | — | — |
| | | glycyrrhetinic acid | — | 470 | — | — | — | — | — | — | — |
| | | isopropyl lauroyl sarcosinate | ELDEW SL-205 | 314 | — | — | — | — | — | — | — |
| | | di(octyldodecyl/phytosteryl/behenyl) lauroyl glutamate | ELDEW PS-306 | 1000 | — | — | — | — | — | — | — |
| | | tranexamic acid | — | 157 | — | — | — | — | — | 0.25 | — |
| | | (phytosteryl/isostearyl/cetyl/stearyl/behenyl) dimer dilinoleate | Plandool-S, H | 1180 | — | — | — | — | — | 0.25 | — |
| | | orange peel extract | CHINPI EXTRACT PM-F | 580 | — | — | — | — | — | — | — |
| | other | isostearic acid | — | — | 0.1 | — | — | — | — | — | — |
| | | sodium hyaluronate | hyaluronic acid HA-Q | — | — | — | — | — | — | — | — |
| II | water | water | — | — | remainder | remainder | remainder | remainder | remainder | remainder | remainder |
| | | (E)/(A) | | | 3 | 1 | 1 | 4 | 2 | 5 | 5 |
| | | (A + B):(C):(D) | | | 10:41.6:6.6 | 10:41.6:6.6 | 10:41.6:6.6 | 10:41.6:6.6 | 10:41.6:6.6 | 10:41.6:6.6 | 10:41.6:6.6 |
| | | O/W emulsion appearance * (immediately after production) | | | ○ | ○ | ○ | ○ | ○ | ○ | ○ |
| | | O/W emulsion appearance (ambient termperature, next day) | | | ○ | ○ | ○ | ○ | ○ | ○ | ○ |
| | | O/W emulsion appearance (ambient termperature, one week later) | | | ○ | ○ | ○ | ○ | ○ | ○ | ○ |
| | | O/W emulsion appearance (ambient termperature, one month later) | | | ○ | ○ | ○ | ○ | ○ | ○ | ○ |

TABLE 3

| Step | Component | Label name | Product name | Average molecular weight of (E) (g/mol) | Ex. 15 | Ex. 16 | Ex. 17 | Ex. 18 | Ex. 19 | Ex. 20 | Ex. 21 |
|---|---|---|---|---|---|---|---|---|---|---|---|
| I | (A) | Polyquaternium-61 | Lipidure-NR | — | 0.1 | 0.1 | 0.1 | 0.1 | 0.1 | 0.1 | 0.1 |
|  | (C) | glycerol, BG |  | — | 1.9 | 1.9 | 1.9 | 1.9 | 1.9 | 1.9 | 1.9 |
|  | (B) | PPG-13 Decyltetradeceth-24 (HLB = 10.7) | UNILUBE 50MT-2200B | — | 0.5 | 0.5 | 0.5 | 0.5 | 0.5 | 0.5 | 0.5 |
|  | (C) | glycerol |  | — | 0.6 | 0.6 | 0.6 | 0.6 | 0.6 | 0.6 | 0.6 |
|  | (D) | water |  | — | 0.4 | 0.4 | 0.4 | 0.4 | 0.4 | 0.4 | 0.4 |
|  | (E) | tocopherol acetate |  | 472 | — | — | — | — | — | — | — |
|  |  | di(phytosteryl/octyldodecyl) lauroyl glutamate | ELDEW PS-203 | 1025 | — | — | — | — | — | — | — |
|  |  | octyldodecyl myristate | octyldodecyl myristate | 500 | — | — | — | — | — | — | — |
|  |  | hydrogenated polyisobutene | PARLAM EX | 490 | — | — | — | — | — | — | — |
|  |  | limonene |  | 136 | — | — | — | — | — | — | — |
|  |  | trisodium ascorbyl palmitate phosphate | Apprecier | 560 | — | — | — | — | — | — | — |
|  |  | glyceryl tri(caprylate/caprate) | Panasate 810 | 465 | — | — | — | — | — | — | — |
|  |  | cyclic lysophosphatidic acid | CyPA-PW | 678 | — | — | — | — | — | — | — |
|  |  | cyclodextrin |  | — | — | — | — | — | — | — | — |
|  |  | ceramide 2 | Ceramide TIC-001 | 555 | 0.5 | — | — | — | — | — | — |
|  |  | glycyrrhizic acid |  | 822 | — | — | — | — | — | — | — |
|  |  | glycyrrhetinic acid |  | 470 | — | 0.3 | — | — | — | — | — |
|  |  | isopropyl lauroyl sarcosinate | ELDEW SL-205 | 314 | — | — | 0.3 | — | — | — | — |
|  |  | di(octyldodecyl/phytosteryl/behenyl) lauroyl glutamate | ELDEW PS-306 | 1000 | — | — | — | 0.5 | — | — | — |
|  |  | tranexamic acid |  | 157 | — | — | — | — | 0.2 | — | — |
|  |  | (phytosteryl/isostearyl/cetyl/stearyl/behenyl) dimer dilinoleate | Plandool-S, H | 1180 | — | — | — | — | — | 0.5 | — |
|  |  | orange peel extract | CHINPI EXTRACT PM-F | 580 | — | — | — | — | — | — | 0.4 |
|  | other | isostearic acid |  | — | — | — | — | — | — | — | — |
|  |  | sodium hyaluronate | hyaluronic acid HA-Q | — | — | — | — | — | — | — | — |
| II | water | water |  |  | remainder | remainder | remainder | remainder | remainder | remainder | remainder |
|  |  | (E)/(A) |  |  | 5 | 3 | 3 | 5 | 2 | 5 | 4 |
|  |  | (A + B):(C):(D) |  |  | 10:41.6:6.6 | 10:41.6:6.6 | 10:41.6:6.6 | 10:41.6:6.6 | 10:41.6:6.6 | 10:41.6:6.6 | 10:41.6:6.6 |
|  |  | O/W emulsion appearance * (immediately after production) |  |  | ○ | ○ | ○ | ○ | ○ | ○ | ○ |
|  |  | O/W emulsion appearance (ambient temperature, next day) |  |  | ○ | ○ | ○ | ○ | ○ | ○ | ○ |
|  |  | O/W emulsion appearance (ambient temperature, one week later) |  |  | ○ | ○ | ○ | ○ | ○ | ○ | ○ |
|  |  | O/W emulsion appearance (ambient temperature, one month later) |  |  | ○ | ○ | ○ | ○ | ○ | ○ | ○ |

TABLE 4

| Step | Component | Label name | Product name | Com Ex. 1 | Com Ex. 2 | Com Ex. 3 | Com Ex. 4 | Com Ex. 5 | Com Ex. 6 |
|---|---|---|---|---|---|---|---|---|---|
| I | (A) | Polyquaternium-61 | Lipidure-NR | 0.1 | 0.1 | 0.2 | 0.1 | — | — |
|  | (C) | glycerol, BG |  | 1.9 | 1.9 | 3.8 | 1.9 | 1.9 | 1.9 |
|  | (A') | Polyquaternium-52 | Synthesis Ex. 1 | — | — | — | — | 0.1 | — |
|  |  | polymethacryloylethyl phosphorylcholine | Synthesis Ex. 2 | — | — | — | — | — | 0.1 |
|  | (B) | PPG-13 Decyltetradeceth-24 | UNILUBE 50MT-2200B | — | — | 0.3 | 0.5 | 0.5 | 0.5 |
|  | (B') | cocoyl arginine ethyl PCA | CAE | — | 0.5 | — | — | — | — |
|  | (C) | glycerol | — | — | — | 0.6 | 0.5 | 0.6 | 0.6 |
|  | (D) | water | — | — | — | 0.4 | 0.2 | 0.6 | .04 |
|  | (E) | tocopherol acetate | — | 0.1 | 0.3 | 0.1 | 0.1 | 0.1 | 0.1 |
| II | water | water | — | remainder | remainder | remainder | remainder | remainder | remainder |
|  |  | (E)/(A) |  | 1 | 3 | 0.5 | 1 | — | — |
|  |  | (A + B):(C):(D) |  | — | — | 10:86:4 | 10:41.6::10 | 10:41.6:6.6 | 10:41.6:6.6 |
|  | O/W emulsion appearance * (immediately after) |  |  | X | X | X | X | X | X |
|  | O/W emulsion appearance (ambient termperature, next day) |  |  | X | X | X | X | X | X |
|  | O/W emulsion appearance (ambient termperature, one week later) |  |  | X | X | X | X | X | X |

TABLE 5

| Step | Component | Label name | Product name | Ex. 22 | Ex. 23 |
|---|---|---|---|---|---|
| I | (A) | Polyquaternium-61 | Lipidure-NR | 0.1 | 0.1 |
|  | (C) | glycerol, BG |  | 1.9 | 1.9 |
|  | (B) | (C12-C14) Pareth-7 (HLB = 12.3) | Nonion NC-207 | 0.5 | — |
|  |  | polyoxyethylene hydrogenated castor oil (HLB = 13.3) | UNIOX HC-40 | — | 0.5 |
|  | (C) | glycerol | — | 0.6 | 0.6 |
|  | (D) | water | — | 0.4 | 0.4 |
|  | (E) | tocopherol acetate | — | 0.3 | 0.3 |
| II | water | water | — | remainder | remainder |
| (E)/(A) |  |  |  | 3 | 3 |
| (A + B):(C):(D) |  |  |  | 10:41.6:6.6 | 10:41.6:6.6 |
| O/W emulsion appearance * (immediately after) |  |  |  | ○ | ○ |
| O/W emulsion appearance (ambient temperature, next day) |  |  |  | ○ | ○ |
| O/W emulsion appearance (ambient temperature, one week later) |  |  |  | ○ | ○ |
| O/W emulsion appearance (ambient temperature, one month later) |  |  |  | ○ | ○ |

TABLE 6

| Step | Component | Label name | Product names | Com Ex. 7 | Com Ex. 8 | Com Ex. 9 | Com Ex. 10 |
|---|---|---|---|---|---|---|---|
| I | (A) | Polyquaterniyum-61 | Lipidure-NR | 0.1 | 0.1 | 0.1 | 0.1 |
|  | (C) | glycerol, BG |  | 1.9 | 1.9 | 3.8 | 1.9 |
|  | (B) | PPG-13 Decyltetradeceth-24 | UNILUBE 50MT-2200B | — | — | — | — |
|  | (B') | Myreth-3 (HLB = 7.6) | Nonion M-203 | 0.5 | — | — | — |
|  |  | (C12-C14) Pareth-3 (HLB = 8.1) | Nonion NC-203 | — | 0.5 | — | — |
|  |  | Myreth-4 (HLB = 9.0) | Nonion M-204 | — | — | 0.5 | — |
|  |  | (C12-C14) Pareth-12 (HLB = 14.6) | Nonion NC-212 | — | — | — | 0.5 |
|  | (C) | glycerol | — | 0.6 | 0.6 | 0.6 | 0.6 |
|  | (D) | water | — | 0.4 | 0.4 | 0.4 | 0.4 |
|  | (E) | tocopherol acetate | — | 0.3 | 0.3 | 0.3 | 0.3 |
| II | water | water | — | remainder | remainder | remainder | remainder |
|  |  | (E)/(A) |  | 3 | 3 | 3 | 3 |
|  |  | (A + B):(C):(D) |  | 10:41.6:6.6 | 10:41.6:6.6 | 10:41.6:6.6 | 10:41.6:6.6 |
| O/W emulsion appearance * (immediately after) |  |  |  | X | X | ○ | X |
| O/W emulsion appearance (ambient termperature, next day) |  |  |  | X | X | X | X |
| O/W emulsion appearance (ambient termperature, one week later) |  |  |  | X | X | X | X |

When polymer nanospheres containing the oily component (E) are formed, the particle size is 300 nm or less, and the appearance of the cosmetic comprising the O/W emulsion is pale and translucent. Accordingly, it is understood from the results in Tables 1 to 3 and 5 that the cosmetics in Examples 1 to 23 are cosmetics containing polymer nanospheres containing large amounts of the various types of oily components (E).

In contrast, in the example in which the component (B) and the component (D) were not included (Comparative Example 1), the example in which the component (B) was replaced with a cationic surfactant (Comparative Example 2), the example in which the ratios of the components (A), (B), (C) and (D) of the emulsification composition were outside of the range of (A)+(B):(C):(D)=1:4 to 8:0.4 to 0.8 (Comparative Example 4), the examples in which the copolymer (A) was a similar copolymer (A') (Comparative Examples 5 and 6), and the examples in which the HLB value of the component (B) was outside of the range of 10 to 14 (Comparative Examples 7 to 10), polymer nanospheres were not formed or the stability was low.

RELATED APPLICATIONS

The present application claims priority on the basis of the Japanese patent application filed on Mar. 13, 2015 (Japanese Patent Application No. 2015-50588), the entire contents of which are incorporated herein by reference.

What is claimed is:

1. A pale and translucent cosmetic obtained by diluting a bicontinuous microemulsion with water,
   wherein the biocontinous microemulsion is obtained by emulsifying a nanoemulsion emulsification composition with an oily component (E),
   wherein the nanoemulsion emulsification composition comprises the following components (A) to (D):
   the component (A) is a copolymer comprising a constitutional unit (a1) of Formula (I) and a constitutional unit (a2) of Formula (2), having the molar ratio of the constitutional unit (a1) to the constitutional unit (a2) from 5:95 to 60:40, and having the weight average molecular weight from 5,000 to 5,000,000;

Formula (I)

$$\left[ -CH_2-\underset{\underset{\underset{O-CH_2-CH_2-O-\underset{\underset{O^-}{\overset{O}{\|}}}{P}-O-CH_2-CH_2-\underset{\underset{CH_3}{|}}{\overset{CH_3}{|}}{N^+}-CH_3}{|}}{\overset{C=O}{|}}}{\overset{R^1}{|}}- \right]$$

wherein $R^1$ is a hydrogen atom or a methyl group;

Formula (II)

$$\left[ -CH_2-\underset{\underset{OR^3}{|}}{\overset{\overset{R^2}{|}}{\underset{C=O}{C}}}- \right]$$

wherein $R^2$ is a hydrogen atom or a methyl group, and $R^3$ is a hydrocarbon group having 12 to 24 carbon atoms;
the component (B) is a nonionic surfactant having an HLB value of 10 to 14;
the component (C) is a polyhydric alcohol; and
the component (D) is water;
and wherein the mass ratios of the components satisfy the following condition:

[(A)+(B)]:(C):(D)=1:4 to 8:0.4 to 0.8.

2. A method for producing a pale and translucent cosmetic, the method comprising:
   (I) mixing a nanoemulsion emulsification composition and an oily component (E) to form a biocontinuous microemulsion,
   wherein the nanoemulsion emulsification composition comprises the following components (A) to (D):
   the component (A) is a copolymer comprising a constitutional unit (a1) of Formula (I) and a constitutional unit (a2) of Formula (2), having the molar ratio of the constitutional unit (a1) to the constitutional unit (a2) from 5:95 to 60:40, and having the weight average molecular weight from 5,000 to 5,000,000;

Formula (I)

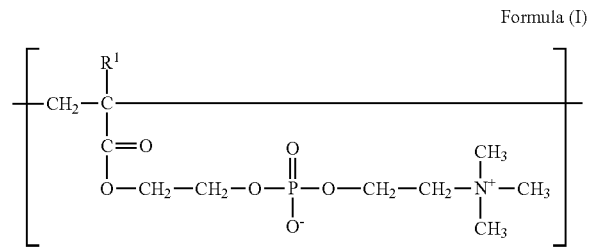

wherein $R^1$ is a hydrogen atom or a methyl group;

Formula (II)

$$\left[ -CH_2-\underset{\underset{OR^3}{|}}{\overset{\overset{R^2}{|}}{\underset{C=O}{C}}}- \right]$$

wherein $R^2$ is a hydrogen atom or a methyl group, and $R^3$ is a hydrocarbon group having 12 to 24 carbon atoms;
the component (B) is a nonionic surfactant having an HLB value of 10 to 14;
the component (C) is a polyhydric alcohol; and
the component (D) is water;
and wherein the mass ratios of the components satisfy the following condition:

[(A)+(B)]:(C):(D)=1:4 to 8:0.4 to 0.8; and (II) diluting the bicontinuous microemulsion obtained in step (I) with water to form the pale and translucent cosmetic.

* * * * *